United States Patent [19]

Ortiz et al.

[11] Patent Number: 5,415,159
[45] Date of Patent: May 16, 1995

[54] SUPPORT STRUCTURE FOR ABDOMINAL LIFT

[75] Inventors: Mark S. Ortiz, Milford; David C. Yates, West Chester, both of Ohio

[73] Assignee: Ethicon, Inc., Cincinnati, Ohio

[21] Appl. No.: 108,431

[22] Filed: Aug. 18, 1993

[51] Int. Cl.$^6$ .......................................... A61B 17/02
[52] U.S. Cl. .................................... 128/20; 248/422; 254/97
[58] Field of Search ........................ 128/20, 17; 606/1; 248/422; 254/95, 97

[56] References Cited

U.S. PATENT DOCUMENTS

| | | |
|---|---|---|
| 925,855 | 6/1909 | Wadsworth ............................ 254/95 |
| 2,599,900 | 6/1952 | Donohue ............................... 254/95 |
| 2,608,192 | 8/1952 | Heitmeyer et al. .................... 128/20 |
| 2,659,965 | 11/1953 | Bailey ..................................... 254/95 |
| 3,196,865 | 7/1965 | Rose ....................................... 128/20 |
| 4,143,652 | 3/1979 | Meier et al. . | 
| 4,379,539 | 4/1983 | Rion et al. ........................ 248/422 X |
| 4,488,209 | 12/1984 | Gosswiller ....................... 248/422 X |
| 4,491,435 | 1/1985 | Meier . |
| 4,796,846 | 1/1989 | Meier et al. . |
| 5,050,586 | 9/1991 | Bonnell ............................ 128/20 X |
| 5,065,739 | 11/1991 | Forrest et al. ......................... 128/20 |
| 5,104,103 | 4/1992 | Auchinleck et al. . |
| 5,109,831 | 5/1992 | Forrest et al. . |
| 5,183,033 | 2/1993 | Wilk . |
| 5,183,465 | 2/1993 | Xanthakos et al. . |

FOREIGN PATENT DOCUMENTS

| | | |
|---|---|---|
| 1092464 | 12/1980 | Canada . |
| 0246086 | 11/1987 | European Pat. Off. . |
| 608367 | 1/1979 | Germany . |
| WO92/21291 | 12/1992 | WIPO . |
| WO92/21294 | 12/1992 | WIPO . |

OTHER PUBLICATIONS

Automated Medical Products Corp. brochure entitled "Iron Intern".
Automated Medical Products Corp. brochure entitled "Abdominal Aortic Aneurysm".
Automated Medical Products Corp. brochure entitled "Anterior Colon Resection".
Automated Medical Products Corp. brochure entitled "Colon Resection".
Automated Medical Products Corp. brochure entitled "Electrocoagulation of Rectal Tumors".
Automated Medical Products Corp. brochure entitled "Kidney Transplants".
Automated Medical Products Corp. brochure entitled "Laparoscopic Surgery".
Automated Medical Products Corp. brochure entitled "Vaginal Hysterectomy".
Davis & Geck Endosurgery brochure entitled "Count On Us".
Andronic Devices Ltd. brochure entitled "Endex Endoscopy Positioning System".
Origin Medsystems, Inc. brochure entitled "Gasless Laparoscopy with Mechanical Peritoneal Distention".
Societe 3X brochure entitled "Le Pneuomoperitoine En Suspension".
Societe 3X brochure entitled "Technical Notes Concerning the Suspender of the Abdominal Wall".
Kitano et al., *A Safe and Simple Method to Maintain a Clear Field of Vision During Laparoscopic Cholecystectomy*, Surg. Endosc., (1992) 6:197–198.
Hashimoto et al., *Laparoscopic Cholecystectomy: An Approach Without Pneumoperitoneum*, Surg. Endosc. (1993) 7:54–56.
Akimuru et al., *Subcutaneous Wire Traction Technique Without $CO_2$ Insufflation for Laparoscopic Cholecystectomy*, Journal of Laparoendoscopic Surgery, (1993), 3:59–62.

Primary Examiner—Richard J. Apley
Assistant Examiner—Donna L. Maraglio
Attorney, Agent, or Firm—Dressler, Goldsmith, Shore & Milnamow, Ltd.

[57] ABSTRACT

A support structure for supporting a surgical instrument is provided. The support structure includes an arm assembly, a leg assembly, a base assembly, and a support bracket. The leg assembly includes a latch mechanism that engages the base assembly. The base assembly includes a gear that engages the leg assembly. An end rail is provided for attachment to the side rails of an operating room bed.

24 Claims, 6 Drawing Sheets

FIG. 6   FIG. 7

SUPPORT STRUCTURE FOR ABDOMINAL LIFT

FIELD OF THE INVENTION

This invention relates generally to surgical instruments and, more particularly, to a support structure for supporting an abdominal lift for use in laparoscopic surgery.

BACKGROUND OF THE INVENTION

Laparoscopic surgical procedures have been around for many years and have recently have become more available due to advances in technology relating to the laparoscope or video imaging system. They are much less intrusive to the patient than typical open surgical procedures. While an open surgical procedure may involve one primary incision that is at least 6-9 centimeters long, a laparoscopic procedure typically uses smaller incisions, each only around 5-11 millimeters in length. In open surgery, the surgeon cuts muscle. In laparoscopic surgery, the surgeon generally does not cut muscle. Because they are less intrusive than open surgical procedures, laparoscopic procedures have resulted in much shorter surgical procedures and recovery times.

Laparoscopic procedures have typically involved insufflation of the abdominal or peritoneal cavity with carbon dioxide and/or other gases in order to create a pneumoperitoneum. The pneumoperitoneum establishes an open space inside the peritoneal cavity to enable the surgeon to move the laparoscope around and see inside.

Typically, the pneumoperitoneum is established by puncturing the abdominal wall with a Veress needle and injecting gas from an insufflator through the Veress needle to a pressure of around 12 mm Hg.

After insufflation, a trocar is advanced through the opening in the abdominal wall and into the peritoneal cavity. The trocar is a tube or cannula that usually has a gaseous seal to contain the carbon dioxide within the peritoneal cavity and maintain insufflation. The cannula is used for insertion of other medical instruments, such as a laparoscope, therethrough and into the peritoneal cavity.

There may be difficulties associated with insufflation of the peritoneal cavity. First and foremost is postoperative pain which patients may experience in the abdomen or shoulder area due to migrating gas. This occurs when insufflation causes excess gas pressure in the peritoneal cavity. Excess gas pressure may also compress the pleural cavities thus making respiration difficult. Other possible difficulties associated with insufflation in laparoscopic surgery include subcutaneous emphysema, blood vessel penetration, etc.

The attendant difficulties of insufflation have led to alternatives to insufflation wherein a pneumoperitoneum is established by elevating the abdominal wall with a mechanical lift. The lift is introduced percutaneously into the peritoneal cavity before establishing a pneumoperitoneum. The lift is elevated mechanically in order to distend the abdomen. When the abdomen is distended, ambient air enters the peritoneum through the puncture opening in the abdomen and a pneumoperitoneum at or near ambient air pressure is established.

By establishing a pneumoperitoneum at ambient air pressure, insufflation and the concomitant need for gaseous seals in endoscopic instruments and trocars for maintaining a relatively high gas pressure in the peritoneal cavity is eliminated. Thus, the attendant difficulties of insufflation, as well as the need for costly equipment, is eliminated.

The prior art includes several abdominal lift devices. In International Patent Application PCT/US92/4456 a lift is disclosed that has two radially extending blades that are rotatable. The blades are closed together for initial insertion into the abdominal cavity. After insertion, the blades are spread or fanned. When the lift is elevated, the blades contact and elevate the inner surface of the abdominal wall.

Societe 3X, a French company, markets an abdominal lift and support structure. The lift is shown and described in International Patent Application Serial No. PCT/FR91/227. The lift includes a series of curves forming a generally triangular shape. The tip of the lift is turned downwardly slightly. The support structure includes a crane and boom design. Gross adjustments are made by sliding the supporting legs and the boom within their respective holders. A mechanical screwjack is used for fine adjustment.

U.S. Pat. No. 5,183,033 describes a method for lifting an abdominal wall with a set of linear and non-linear abdominal lifts. International Patent Application PCT/U.S. No. 92/4392 describes a variety of mechanical rods, arms and/or balloons for mechanically lifting an abdominal wall during laparoscopic surgery.

There are some other prior art structures for elevating and/or supporting abdominal lifts in laparoscopic surgery. U.S. Pat. No. 5,183,033 illustrates support structures using winches or U-shaped bars for use in laparoscopic surgery.

Further, there are a number of prior art support structures for supporting mechanical lifts used in open surgery. For example, see U.S. Pat. Nos. 5,109,831 and 4,143,652.

The adjustment capabilities of these prior art devices are limited. It would be desirable to provide a support structure for holding an abdominal lift in an elevated position that is mechanically operable by the surgeon at the operating room table and has a variety of position adjustments. It would be desirable to provide a mechanical lift adjustment having both gross and fine adjustment capabilities and can be adjusted for left or right-handed operation. Also, it would be desirable to provide a latch mechanism associated with the lift mechanism wherein a leg assembly of the support structure automatically engages a base in order to fix the height of the abdominal lift.

SUMMARY OF THE INVENTION

The support structure for holding an abdominal lift in accordance with the invention is mechanically operable by the surgeon at an operating room table and has a variety of position adjustments. It has a mechanical lift adjustment for both gross and fine adjustment which can be adjusted for left or right-handed operation.

The support structure is detachably and slidably attachable to an operating room table. It includes a support bracket that attaches to the side rails of an operating room table. In an alternative aspect of the invention, an end rail is provided for attachment to the side rails of an operating room table and the support bracket is detachably and slidably connectable to the end rail. Thus, the support structure can be positioned at the end of an operating room table.

An upstanding leg assembly is rotatably and slidably attached to the support bracket. An arm assembly is rotatably and slidably connected to the leg assembly. The distal end of the arm assembly has a holding portion for holding an abdominal lift.

The leg assembly includes a gear rack member which is engageable with a gear member. The gear member is held by a gear brace that is connected to the support bracket. The gear member ratchets for vertical adjustment of the leg assembly.

The gear rack member is movable between an engaged position wherein the gear rack member is engaged with the gear member and a disengaged position wherein the gear rack member is disengaged from the gear member. When the gear rack member and gear member are engaged, then the leg assembly is prevented from sliding downwardly relative to the support bracket. When the gear rack member is disengaged from the gear member, the leg assembly slides freely relative to the support bracket for gross vertical adjustment.

A spring biases the gear rack member toward the engaged position. Thus, the gear rack member is automatically engaged with the gear member.

The gear rack member is movable within a gear jacket inside the leg assembly. The jacket has a pin that coacts with a cam portion on the gear rack member in order to move the gear rack member between the engaged position and disengaged position.

The gear brace is rotatable relative to the support bracket whereby the gear brace and gear member can be adjusted for either left or right-handed operation.

In an alternative aspect of the invention, the holding portion of the arm assembly includes a force measuring gauge for monitoring and controlling the lift force on the surgical device being held by the support structure.

These and other aspects and attributes of the present invention will be discussed with reference to the following drawings and accompanying specification.

DETAILED DESCRIPTION OF THE INVENTION

The following is a detailed description of the invention. The detailed description is not intended to be an exhaustive description of all embodiments within the scope of the invention and is not intended to limit the scope of the claims to the disclosed embodiments. Other embodiments within the scope of the claims will be apparent to those skilled in the art.

Figure 1:
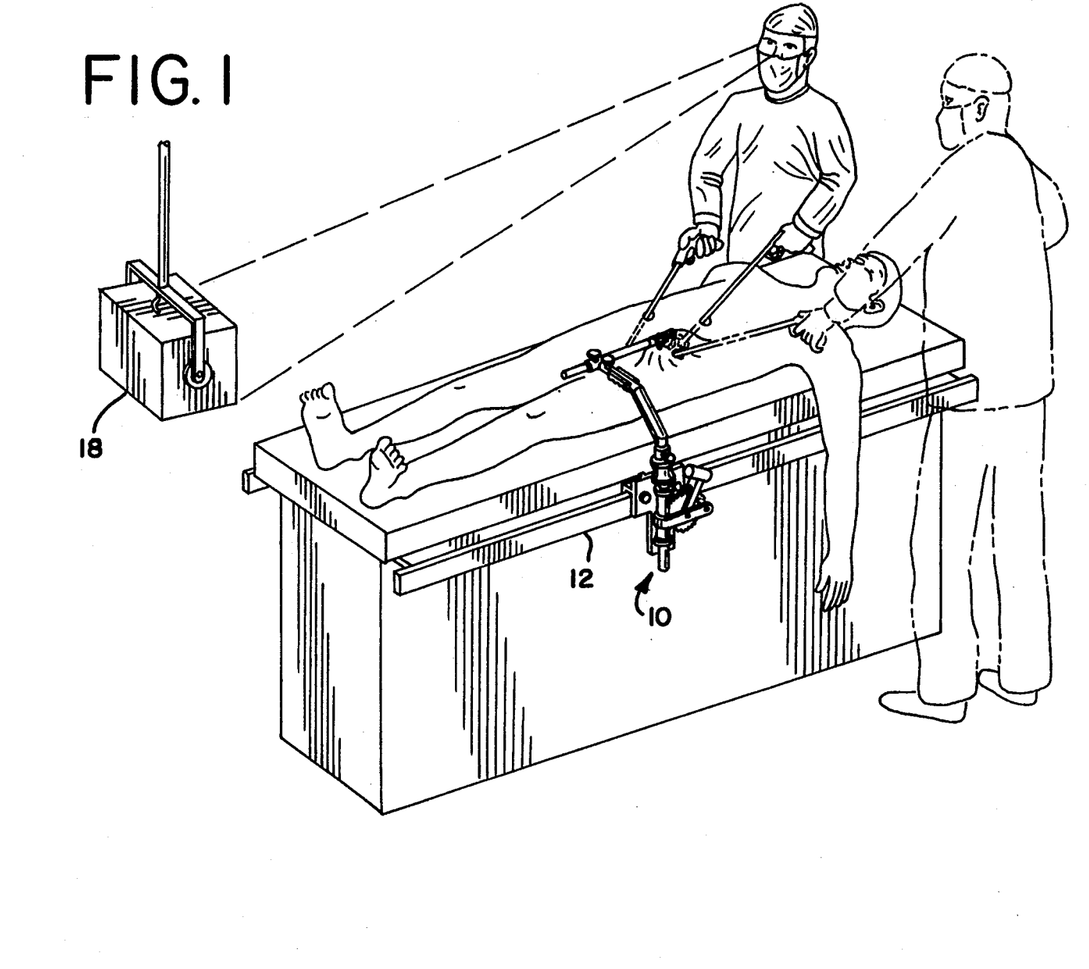
FIG. 1 is a perspective view of a support structure for supporting an abdominal lift in accordance with the invention wherein the support structure is attached to the side rail of an operating room bed and supports an abdominal lift during laparoscopic surgery.

Referring to FIG. 1, a support structure 10 for supporting an abdominal lift in accordance with the invention is shown. The support structure 10 is clamped to the side rail 12 of an operating room table. The support structure as shown is supporting an abdominal lift during laparoscopic surgery. The two surgeons are inserting a laparoscope and laparoscopic surgical instruments into a pneumoperitoneum established by the abdominal lift. The surgeons view a monitor 18 which displays the view seen by the laparoscope.

Figure 2:
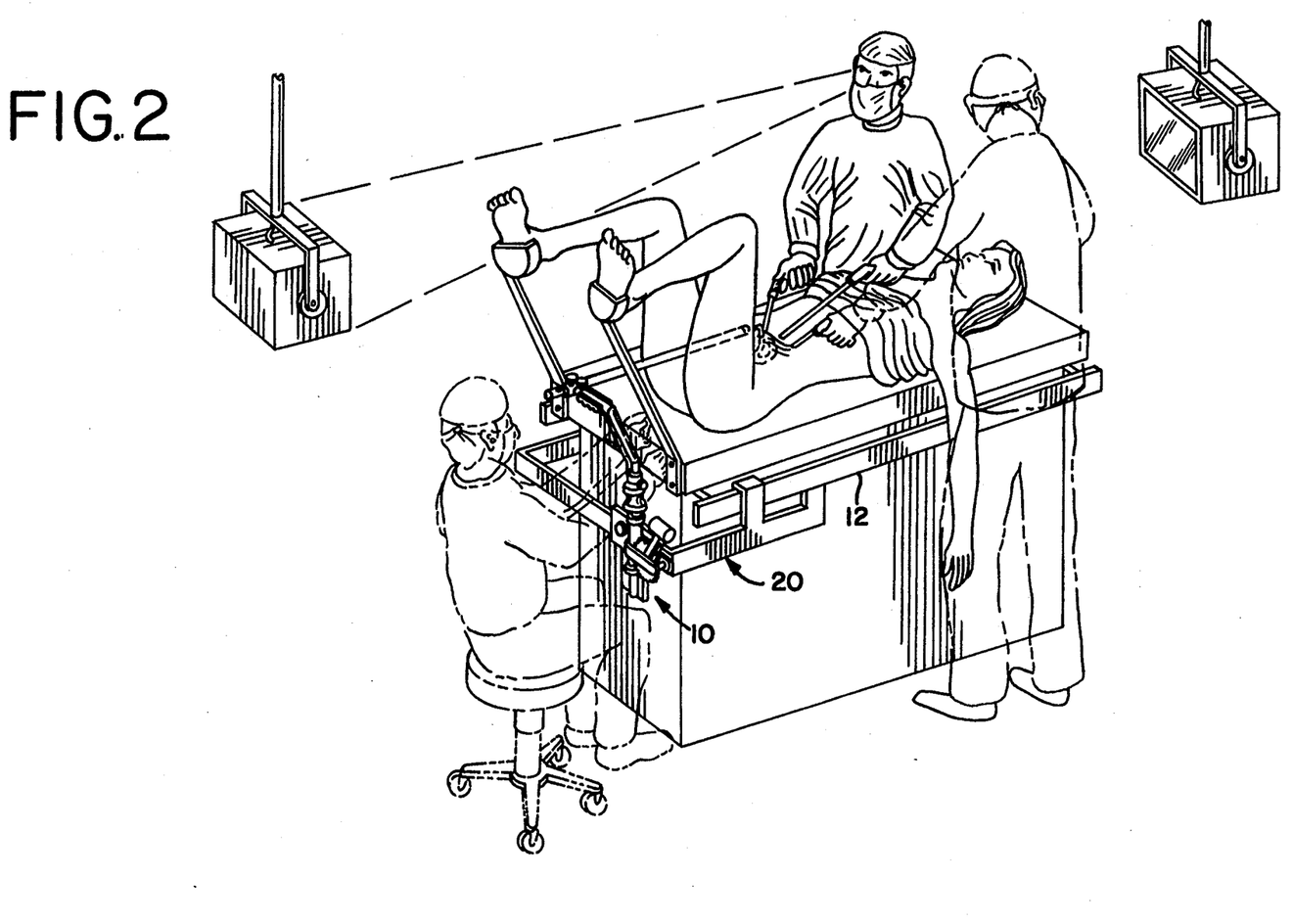
FIG. 2 is a perspective view of a support structure for supporting an abdominal lift in accordance with the invention including an end rail wherein the support structure is connected to the end rail and supports an abdominal lift during a laparoscopic surgery.

Referring to FIG. 2, a support structure 10 for supporting an abdominal lift is clamped on an end rail 20 which is attachable to the side rails 12 of the operating room table. Thus, the support structure 10 may be mounted at the end of the operating room table to gain access to the patient from the end of the table.

Figures 3, 4:
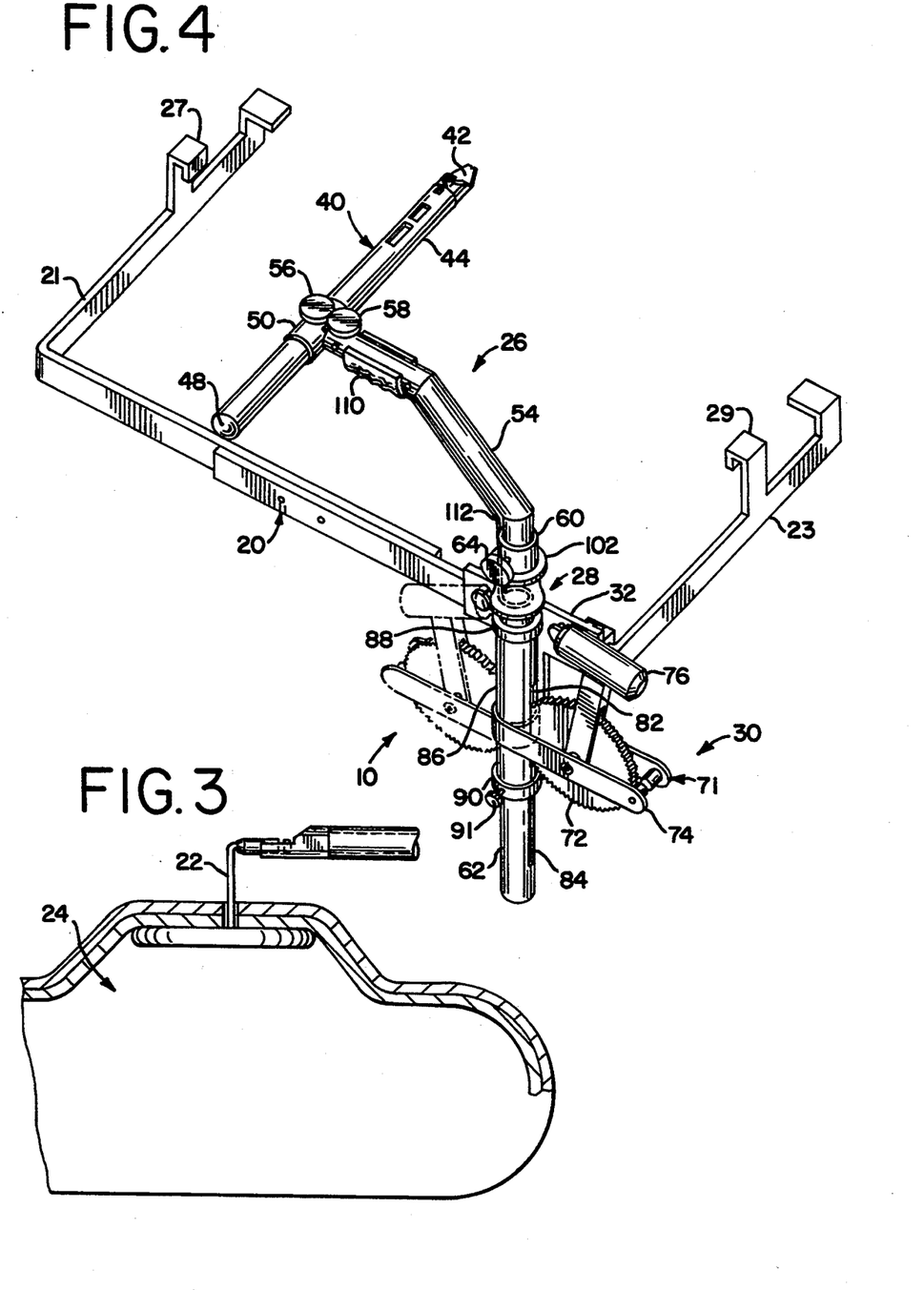
FIG. 3 is an elevational view of a portion of the arm assembly of the support structure attached to an abdominal lift that is inserted into the abdomen.
FIG. 4 is an enlarged perspective view of the support structure as shown in FIG. 2.

Referring to FIG. 3, a preferred use of the support structure 10 is to elevate and support an abdominal lift 22. The abdominal lift 22 shown in FIG. 3 is of the type described in detail in copending patent application Ser. No. 08/108,895, entitled Abdominal Lift Device, the disclosure of which is incorporated by reference herein. The cavity under the lift is a pneumoperitoneum 24 providing a work area for laparoscopic surgery.

Referring to FIG. 4, the support structure in accordance with the invention includes an arm assembly 26, a leg assembly 28 and a base assembly 30.

Figure 5:
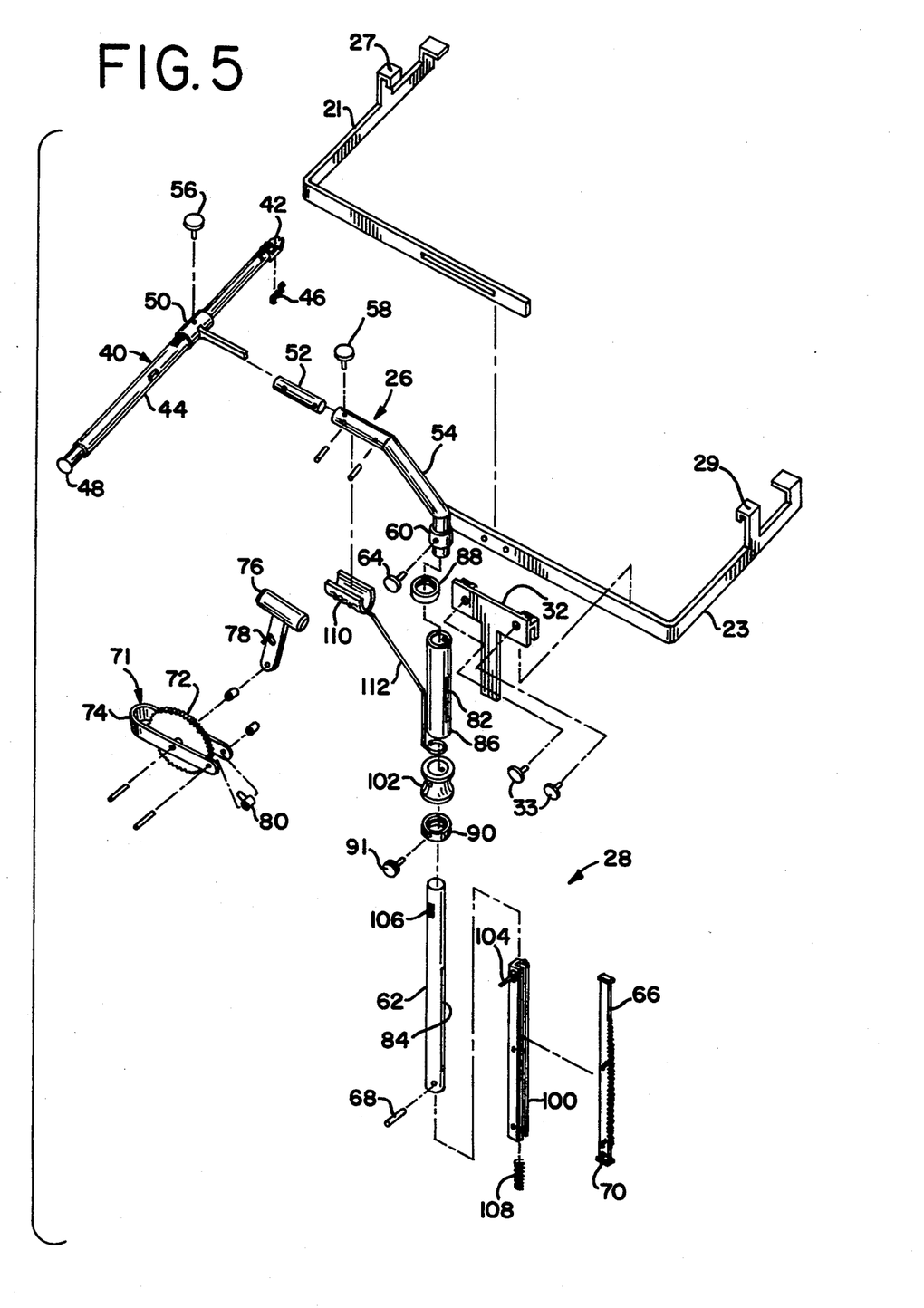
FIG. 5 is an exploded view of the support structure shown in FIG. 4.

The base assembly 30 includes a support bracket 32 is connectable to either a side rail 12 of an operating room table or an end rail 20 as shown in FIGS. 2, 4 and 5. Referring to FIG. 5, tightening knobs 33 are threaded through the support bracket 32 to clamp down on the side rail 12 or end rail 20 in order to hold the support bracket 32 in place. The end rail 20 is constructed from two halves 21 and 23 that are connected to each other. Hangers 27 and 29 are provided on the two halves 21 and 23 for hanging the end rail 20 on the side rails 12 of an operating room bed as shown in FIG. 2.

Referring to FIGS. 4 and 5, the arm assembly 26 includes a holding portion 40. The holding portion 40 has a detachable tip 42 which is inserted into a shaft 44. A clip 46 is used to fasten the tip 42 to the shaft 44. The shaft 44 has an end cap 48. The shaft 44 is rotatably held by a collar 50 that is inserted into a slotted retaining member 52 that fits within the distal end of arm portion 54.

A tightening knob 56 is threaded into the collar 50 in order to tighten down and hold the shaft 44 within the collar 50. A tightening knob 58 is insertable into the arm portion 54 in order to tighten down and hold the slotted retaining member 52 within the arm portion 54.

The arm portion 54 extends upwardly from the leg assembly 28. The arm portion 54 is bent in two places at 45° angles. Thus, the distal end of the arm portion 54 is oriented at a 90° angle relative to the proximal end of the arm portion 54 and the distal end of the arm portion 54 extends horizontally.

Figures 6, 7:
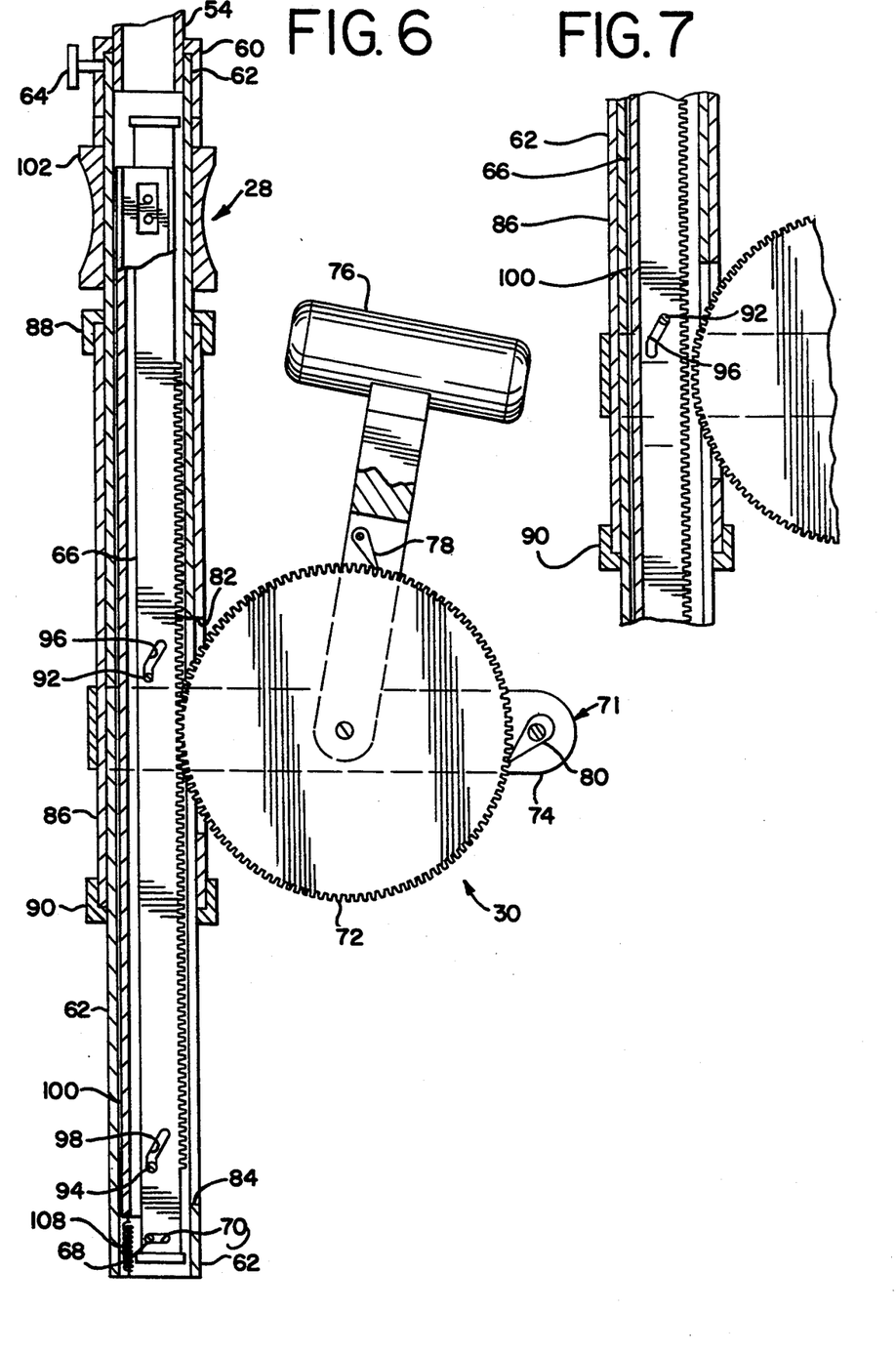
FIG. 6 is an elevational view, shown in partial cross-section, of the leg assembly and gear assembly of the support structure.
FIG. 7 is an elevational view, shown in partial cross-section, of a portion of the leg assembly with the gear inserted therein.

The bottom of the arm assembly 26 is connected to the top of the leg assembly 28 (FIGS. 4 and 5). The bottom of the arm portion 54 has a collar 60 that receives an upwardly extending tube 62 that is part of the leg assembly 28. As shown in FIG. 6, the upper end of the tube 62 is slidably inserted between the collar 60 and the arm portion 54 and abuts the collar 60. A tightening knob 64 is threaded into the collar 60 in order to tighten down on and hold the tube 62. When the tightening knob 64 is loosened, the arm portion 54 may be rotated relative to the tube 62 in order to rotate the arm assembly 26 relative to the leg assembly 28.

Referring to FIGS. 5 and 6, a gear rack 66 extends within the tube 62. A horizontal slot 70 in the gear rack 66 receives a pin 68 extending across the diameter of the tube 62 at its bottom end. The pin 68 and slot 70 cooperate to restrict vertical motion and permit horizontal motion of the gear rack 66 relative to the tube 62. Thus, when the gear rack 66 is raised by the gear 72 as discussed below, the tube 62 and entire leg assembly 28 are carried with it.

Referring to FIGS. 4–6, the gear rack 66 is actuated by a gear assembly 71. The gear assembly 71 includes a gear 72 and crank 76 rotatably mounted on a gear brace 74. A spring loaded pawl 78 on the crank 76 and a spring loaded ratchet 80 on the gear brace 74 cooperate with the gear 72 in order to crank the gear 72 clockwise and prevent counter-clockwise rotation.

As shown in FIG. 6, the gear 72 extends through a slot 84 in the tube 62 and engages the gear rack 66. By rotating the crank 76 clockwise, the gear 72 is rotated clockwise and the gear rack 66 is ratcheted in an upward direction. Thus, the gear assembly 71 functions as a lift mechanism that lifts the leg assembly 28 and provides a fine height adjustment.

Referring to FIGS. 4 and 5, the leg assembly 28 is slidably contained within a tubular member or can 86. The can 86 is contained between two swivel rings 88 and 90 which are welded to the support bracket 32. The gear brace 74 is welded to the can 86. Thus, the gear 72, gear brace 74, can 86, swivel rings 88 and 90 and support bracket 32 are connected together and form a base assembly 30 which receives the leg assembly 28.

The swivel rings 88 and 90 permit the can 86 to rotate relative to the support bracket 32. The can 86 defines a slot 82 that permits the gear 72 to extend through to engage the gear rack 66 inside the leg assembly 28. When the gear assembly 71 is rotated from a right-handed orientation as shown in solid lines in FIG. 4, to a left-handed orientation as shown in phantom lines in FIG. 4, the can 86, tube 62 and gear rack 66 are all rotated with the gear assembly 71. A tightening knob 91 is threaded into one of the rings 90 for tightening down on and holding the can 86 in order to prevent it from rotating.

The gear rack 66 is movable within the tube 62 between an engaged position as shown in FIG. 6 and a disengaged position as shown in FIG. 7. When the gear rack 66 is engaged with the gear 72, the leg assembly 28 cannot move downwardly because the gear 72 is restricted by the pawl 80. Thus, the gear rack 66 functions as a latch mechanism for latching the leg assembly 28 to the base assembly 30 and preventing downward movement of the leg assembly 28. When the gear rack 66 is disengaged, then the leg assembly 28 is released and free to move upwardly or downwardly relative to the base assembly 30 for gross height adjustment.

The gear rack 66 is adjusted between its engaged and disengaged positions by vertical movement of a pair of camming pins 92 and 94 extending within a pair of camming slots 96 and 98 in the gear rack 66. The camming pins 92 and 94 are rigidly connected to a gear jacket 100 that envelopes the gear rack 66 inside the tube 62.

The gear jacket 100 is vertically slidable within the tube 62. The jacket 100 is connected to an adjust collar 102 through a pin 104 (FIG. 5) that extends through a vertically extending slot 106 in the tube 62. The slot 106 permits the pin 104 to slide vertically within it. The adjust collar 102 wraps around the tube 62 and is vertically slidable relative to the tube 62. Thus, the gear jacket 100 can be moved in a vertical direction by vertical movement of the adjust collar 102.

When the adjust collar 102 and gear jacket 100 are lifted, the camming pins 92 and 94 are lifted upwardly within the camming slots 96 and 98 and thereby disengage the gear rack 66 from the gear 72, as shown in FIG. 7. When the adjust collar 102 and gear jacket 100 are lowered, the camming pins 92 and 94 are lowered within the camming slots 96 and 98 and thereby cause the gear rack 66 to engage the gear 72 as shown in FIG. 6.

Referring to FIGS. 5 and 6, a spring 108 extending from the bottom of the jacket 100 to the tube 62 biases the jacket 100 to a lowered position relative to the tube 62 wherein the gear rack 66 is engaged with the gear 72. Thus, when the adjust collar 102 is released after having been manually lifted for gross vertical adjustment of the leg assembly 28, the gear jacket 100 snaps downwardly and the gear rack 66 and gear 72 are immediately and automatically engaged.

Referring to FIGS. 4 and 5, a handgrip 110 and lift wire 112 may be provided on the arm portion 54 for lifting the adjust collar 102. The lift wire 112 extends downwardly and wraps around the tube 62 underneath the adjust collar 102. When the handgrip 110 is squeezed and pulled upwardly, it raises the lift wire 112 which in turn raises the adjust collar 102. Thus, the handgrip 110 can be operated with one hand to disengage the gear rack 66 and gear 72 for gross vertical adjustment of the leg assembly 28.

Figure 8:
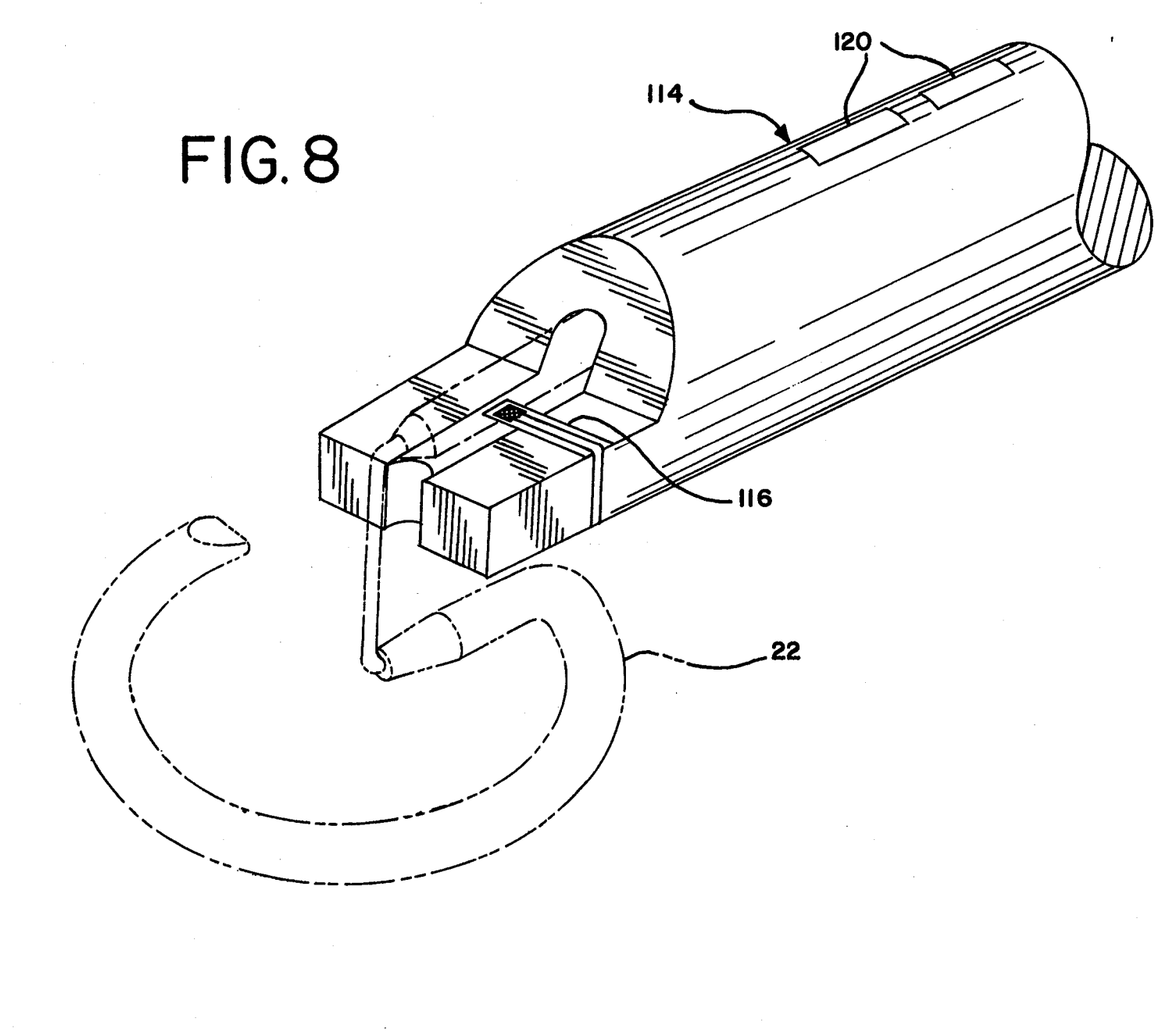
FIG. 8 is a partial perspective view of an alternative holding portion and force measuring gauge in accordance with the invention.

Referring to FIG. 8, an alternative holding portion 114 may optionally include a force measuring gauge 116 that is calibrated to show the lifting force being applied to a surgical device 22 that is suspended from the holding portion 114. Preferably, the force measuring gauge is either a conventional strain gauge, piezoelectric gauge or semi-conductor strain gauge. For use in supporting an abdominal lift, the gauge is preferably calibrated to show lifting forces in the range of 0 to 25 pounds. The lift force is preferably displayed on the holding portion 114. As shown in FIG. 8, there are two windows 120 wherein one window is a conventional bar graph display of relative force and the other window is a conventional numerical display of force in pounds, kilograms, etc.

During use as shown in FIGS. 1 and 2, the support structure 10 may be used in a variety of surgical applications. In particular, the support structure may be used to support an abdominal lift 22 during endoscopic surgery. Fine adjustment of the elevation of the abdominal lift may be accomplished by ratcheting the support structure 10 upwardly. For gross adjustment, the adjust collar 102 is lifted to disengage the gear rack from the gear and permit the entire support structure to be manually raised and lowered.

What is claimed is:

1. A surgical instrument support structure comprising:
   a support bracket;
   an elongated leg assembly slidably connected to said support bracket for longitudinal movement with respect thereto, said leg assembly including a gear rack member;
   a gear brace connected to said support bracket, said gear brace being rotatable relative to said support bracket;
   a gear member rotatably connected to said gear brace, said gear member being selectively engageable with said gear rack member;
   a ratchet mechanism engageable with said gear member for controlling the rotation of said gear member; and
   an arm assembly extending from said leg assembly for holding a surgical instrument.

2. A surgical instrument support structure in accordance with claim 1 including a crank engageable with said gear member for rotation thereof.

3. A surgical instrument support structure in accordance with claim 2 wherein said crank includes a pawl that is engageable with said gear member.

4. A surgical instrument support structure in accordance with claim 1 wherein said arm assembly is rotatable relative to said leg assembly.

5. A surgical instrument support structure in accordance with claim 1 wherein said gear rack member is movable between an engaged position wherein said gear rack member is engaged with said gear member and a disengaged position wherein said gear rack member is disengaged from said gear member.

6. A surgical instrument support structure in accordance with claim 5 including a jacket member extending longitudinally adjacent said gear rack member.

7. A surgical instrument support structure in accordance with claim 6 wherein said jacket member has at least one pin and said gear rack member has at least one cam portion that coacts with said pin.

8. A surgical instrument support structure in accordance with claim 5 including an external adjustment collar connected to said gear rack member for moving said gear rack member between said engaged position and said disengaged position.

9. A support structure in accordance with claim 8 including an adjustment handgrip that is connected to said adjustment collar.

10. A support structure in accordance with claim 9 wherein said handgrip is configured for one-handed operation.

11. A surgical instrument support structure comprising:
    a support bracket;
    an elongated leg assembly slidably connected to said support bracket for longitudinal movement with respect thereto, said leg assembly including a gear rack member;
    a gear brace connected to said support bracket;
    a gear member rotatably connected to said gear brace, said gear member being selectively engageable with said gear rack member, said gear rack member being movable between an engaged position wherein said gear rack member is engaged with said gear member and a disengaged position wherein said gear rack member is disengaged from said gear member;
    a jacket member extending longitudinally adjacent said gear rack member, said jacket member having at least one pin and said gear rack member having at least one cam portion that coacts with said pin;
    a ratchet mechanism engageable with said gear member for controlling the rotation of said gear member; and
    an arm assembly extending from said leg assembly for holding a surgical instrument.

12. A surgical instrument support structure in accordance with claim 11 wherein said pin is movable relative to said cam portion between an engaged position wherein said gear rack member is engaged with said gear member and a disengaged position wherein said gear rack is disengaged from said gear.

13. A surgical instrument support structure comprising:
    a support bracket;
    an upwardly extending leg assembly having a longitudinal axial and slidably connected to said support bracket, said leg assembly being selectively movable between a raised position and a lowered position;
    a gear assembly connected to said support bracket, said gear assembly being rotatable about said longitudinal axis of said leg assembly, gear assembly including a gear member that is engageable with said leg assembly for Selective movement of said leg assembly between said raised position and said lowered position; and
    an arm assembly extending from said leg assembly, said arm assembly including a holding portion for holding a surgical instrument.

14. A surgical instrument support structure in accordance with claim 13 wherein said support bracket is detachably connectable to an operating room bed side rail.

15. A surgical instrument support structure in accordance with claim 14 including an end rail that is connectable to an operating room bed, said support bracket being detachably connectable to said end rail.

16. A surgical instrument support structure in accordance with claim 13 wherein said leg assembly includes a gear rack member that is engageable with said gear member.

17. A surgical instrument support structure in accordance with claim 16 wherein said gear rack member is movable between an engaged position and a disengaged position.

18. A surgical instrument support structure in accordance with claim 17 including a jacket extending longitudinally adjacent said gear rack.

19. A surgical instrument support structure in accordance with claim 18 wherein said jacket has at least one pin and said gear rack member has at least one cam portion that is engageable with said pin.

20. A surgical instrument support structure in accordance with claim 19 wherein said pin is movable relative to said cam portion between an engaged position wherein said gear rack member is engaged with said gear member and a disengaged position wherein said gear rack member is disengaged with said gear member.

21. A surgical instrument support structure in accordance with claim 13 wherein said gear assembly includes a ratcheting crank mechanism for adjusting said movement of said leg assembly.

22. A surgical instrument support structure in accordance with claim 13 including a force measuring gauge connected to said holding portion.

23. A surgical instrument support structure comprising:

a support bracket;

an upwardly extending leg assembly slidably connected to said support bracket, said leg assembly being selectively movable between a raised position and a lowered position;

a gear assembly connected to said support bracket, said gear assembly including a gear member that is engageable with said leg assembly for selective movement of said leg assembly between said raised position and said lowered position, said leg assembly including a gear rack member that is engageable with said gear member, said gear rack member being movable between an engaged position and a disengaged position;

a jacket extending longitudinally adjacent said gear rack, said jacket having at least one pin and said gear rack member having at least one cam portion that is engageable with said pin; and an arm assembly extending from said leg assembly, said arm assembly including a holding portion for holding a surgical instrument.

24. A surgical instrument support structure, comprising:

a support bracket;

an upwardly extending leg assembly slidably connected to said support bracket, said leg assembly including a gear rack member that is selectively movable between a raised position and a lowered position;

a gear assembly connected to said support bracket, said gear assembly including a rotatably mounted gear member that is engageable with said gear rack member for selective movement of said leg assembly between said raised position and said lowered position, said gear rack member being selectively movable between a position in engagement with said gear member and a position in disengagement with said gear member, said gear rack member being spring biased toward a position in engagement with said gear member; and an arm assembly extending from said leg assembly, said arm assembly including a holding portion for holding a surgical instrument.

* * * * *